US008975087B2

(12) United States Patent
Nelson et al.

(10) Patent No.: US 8,975,087 B2
(45) Date of Patent: Mar. 10, 2015

(54) LONGITUDINAL ASSAY

(75) Inventors: James Curtis Nelson, Raleigh, NC (US); David Ure, Wellesley, MA (US)

(73) Assignee: Inanovate, Inc., Research Triangle Park, NC (US)

( * ) Notice: Subject to any disclaimer, the term of this patent is extended or adjusted under 35 U.S.C. 154(b) by 568 days.

(21) Appl. No.: 12/956,117

(22) Filed: Nov. 30, 2010

(65) Prior Publication Data

US 2012/0129271 A1    May 24, 2012

(51) Int. Cl.
   *G01N 33/543*   (2006.01)
   *F04B 43/00*    (2006.01)
   *F04B 43/02*    (2006.01)
   *F04B 43/04*    (2006.01)
   *F04B 43/06*    (2006.01)

(52) U.S. Cl.
   CPC .......... *F04B 43/0009* (2013.01); *F04B 43/02* (2013.01); *F04B 43/04* (2013.01); *F04B 43/06* (2013.01)
   USPC .......... 436/518; 435/7.1; 435/7.92; 435/7.93; 435/7.94; 436/501

(58) Field of Classification Search
   None
   See application file for complete search history.

(56) References Cited

U.S. PATENT DOCUMENTS

| | | | |
|---|---|---|---|
| 4,012,178 A | 3/1977 | Puckett | |
| 5,074,765 A | 12/1991 | Pekar | |
| 5,089,387 A * | 2/1992 | Tsay et al. | 435/6.11 |
| 5,372,487 A | 12/1994 | Pekar | |
| 6,382,923 B1 | 5/2002 | Gray | |
| 6,908,594 B1 | 6/2005 | Schaevitz et al. | |
| 2004/0191818 A1* | 9/2004 | O'Toole et al. | 435/6 |
| 2005/0033520 A1 | 2/2005 | Dai et al. | |
| 2006/0263907 A1* | 11/2006 | Zweig | 436/524 |
| 2007/0074972 A1 | 4/2007 | Nassef et al. | |
| 2008/0199482 A1* | 8/2008 | Dijkstra et al. | 424/174.1 |
| 2009/0192410 A1 | 7/2009 | Freeman et al. | |
| 2009/0305332 A1 | 12/2009 | Haendler et al. | |
| 2010/0298684 A1 | 11/2010 | Leach et al. | |
| 2011/0020918 A1 | 1/2011 | Nassef et al. | |
| 2011/0092389 A1 | 4/2011 | Dickinson et al. | |
| 2011/0257732 A1 | 10/2011 | McClain et al. | |
| 2011/0262896 A1 | 10/2011 | Blecka et al. | |
| 2012/0282684 A1 | 11/2012 | Fritchie et al. | |

FOREIGN PATENT DOCUMENTS

| | | |
|---|---|---|
| EP | 2273404 A1 | 1/2011 |
| WO | 9310455 A1 | 5/1993 |
| WO | 2006101550 A1 | 9/2006 |
| WO | 2012007783 A1 | 1/2012 |
| WO | 2012037369 A1 | 3/2012 |

OTHER PUBLICATIONS

Wang et al., Pre-binding dynamic range and sensitivity for immunosensors using nanofluidic preconcentrator, Lab Chip, 2008, 8, pp. 392-394.*
Peytavi et al., Microfluids Device for Rapid Automated Micrarray Hybridization, Clinical Chemistry 51:10, 2005, pp. 1836-1844.*
Patent Cooperation Treaty, PCT Notification of Transmittal of International Search Report and the Written Opinion of the International Searching Authority, or the Declaration dated Jul. 22, 2011 for PCT/US2010/058112, 14 pages, Jul. 22, 2013.
Dai et al., "Use of Hybridization Kinetics for Differentiating Specific From Non-Specific Binding to Oligonucleotide Microarrays," dated May 2002, pp. 1-8, Nucleic Acids Research, vol. 30, No. 16.
Furusawa et al., "Model-Based Analysis of Non-Specific Binding for Background Correction of High-Density Oligonucleotide Microarrays," Oct. 2008, pp. 36-41, Bioinformatics, vol. 25, No. 1.
Patent Cooperation Treaty, Notification of Transmittal of the International Search Report and the Written Opinion of the International Searching Authority for PCT/US2011/030240 datd Sep. 27, 2011, 14 pages, Sep. 27, 2011.
Patent Cooperation Treaty, Notification of Transmittal of International Preliminary Report on Patentability for PCT/US2011/030240 dated May 28, 2013, 9 pages, May 28, 2013.
Patent Cooperation Treaty, PCT Notification of Transmittal of International Preliminary Report on Patentability and the Written Opinion of the International Searching Authority dated Jun. 6, 2013 for PCT/US2010/058112, 9 pages, Jun. 6, 2013.
Patent Cooperation Treaty, Notification of Transmittal of the International Search Report and the Written Opinion of the International Searching Authority for PCT/US2014/24396 mailed Jul. 8, 2014, 34 pages, Jul. 8, 2014.
Burry, "Controls for Immunocytochemistry: An Update," 2011, pp. 6-12, Journal of Histochemistry & Cytochemistry, Jan. 2011.
SIGMA Life Science, "qPCR Technical Guide," retrieved May 23, 2014 at http://www.sigmaaldrich.com/life-science/molecular-biology/pcr/quantitative-pcr/qpcr-technical guide.html, pp. 1-40, May 23, 2014.

* cited by examiner

*Primary Examiner* — Gary W Counts

(74) *Attorney, Agent, or Firm* — Hoffman Warnick LLC

(57) ABSTRACT

Embodiments of the invention include methods for detecting and determining the concentrations of macro and small molecules, including bio-molecules, in a liquid or gaseous sample.

17 Claims, 10 Drawing Sheets

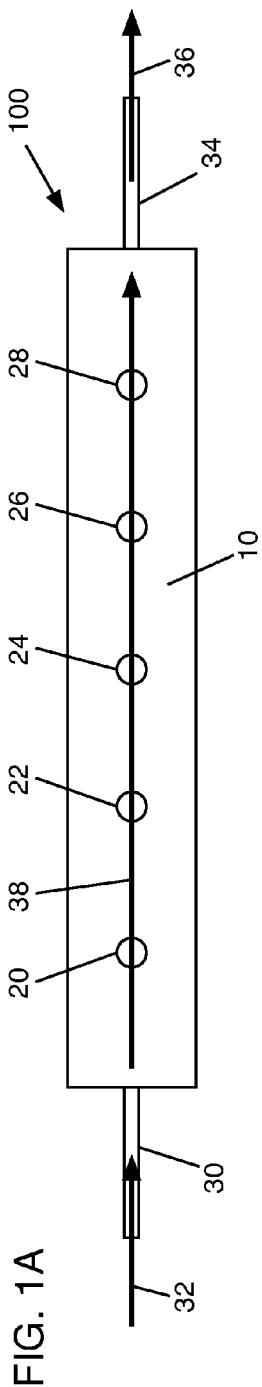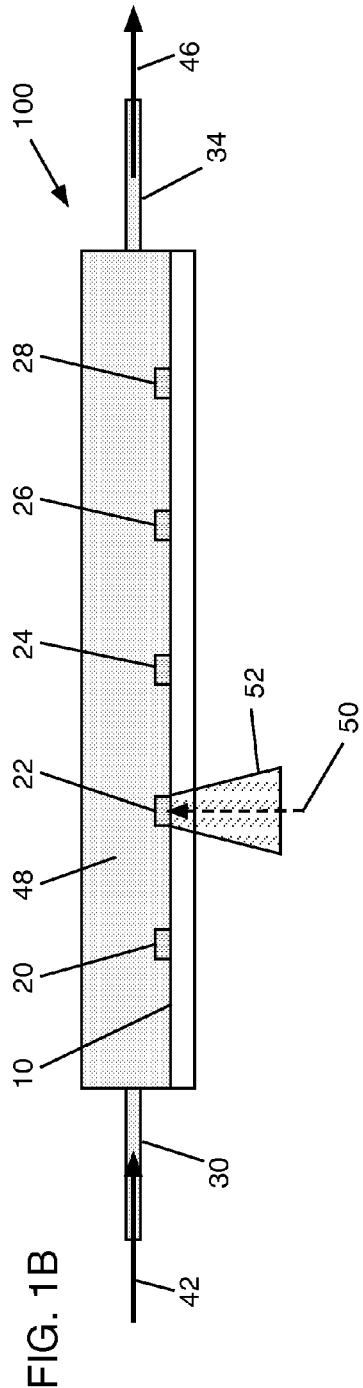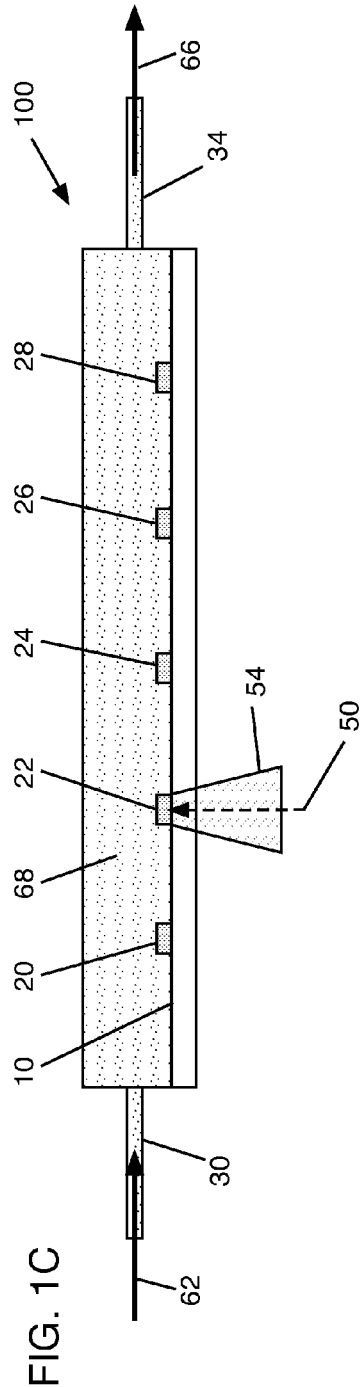

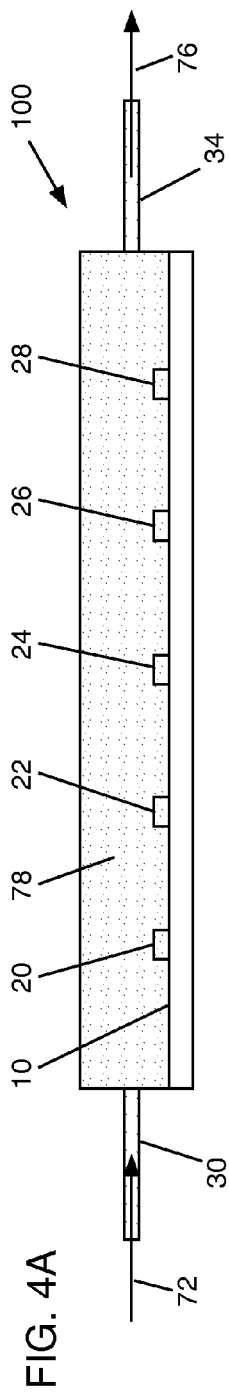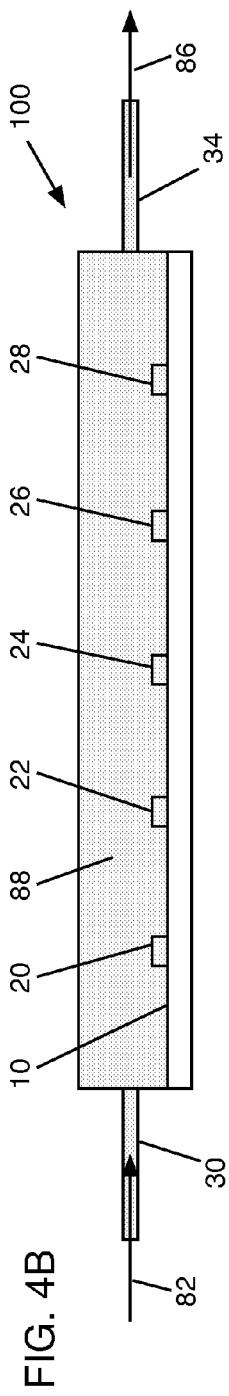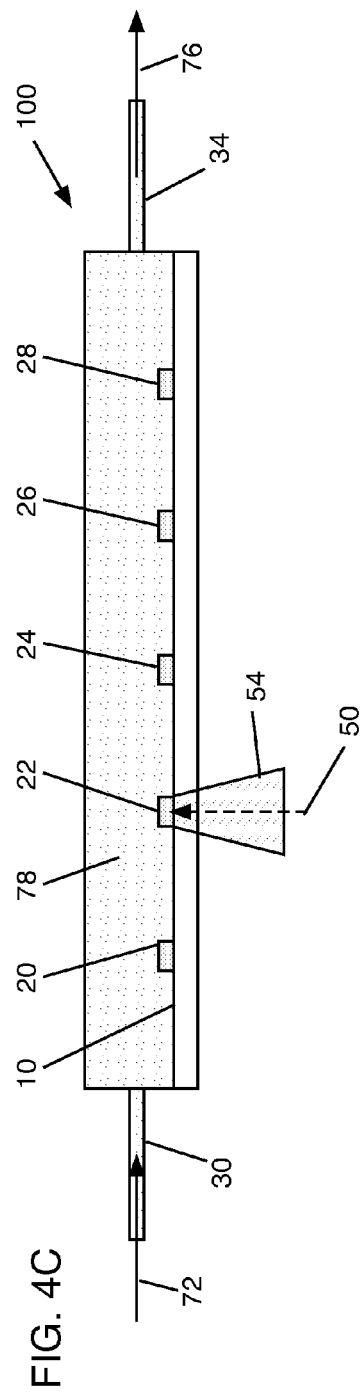

US 8,975,087 B2

LONGITUDINAL ASSAY

CROSS-REFERENCE TO RELATED APPLICATIONS

This application claims the benefit of co-pending International Patent Application No. PCT/US10/58112, filed 24 Nov. 2010, which is hereby incorporated herein.

BACKGROUND OF THE INVENTION

Many areas of research and clinical practice employ various detection methods and technologies for detecting and measuring concentrations of macro and small molecules, including bio-molecules. Often, it is desirable to perform such detection with great sensitivity, quickly, and/or in a multiplex. Known methods, however, typically sacrifice one or more features in favor of another, depending on the context in which the method is employed.

For example, multiplexed assays typically involve detection of all analytes after a single period of elapsed time. This period is often chosen based on the optimal binding kinetics of one analyte of a plurality of analytes, which necessarily results in detection at a time that is not optimal for the other analytes, based on their binding kinetics. Similarly, known methods may sacrifice the sensitivity of an assay in favor of obtaining a rapid result, or vice versa.

A significant limitation of known assay methods is their inability to distinguish specific binding of an analyte from non-specific binding of non-analyte components of a tested sample. Biological samples, for example, may contain a high concentration of proteins that are not of interest, relative to the concentration of a protein that is of interest, but which may still engage in non-specific binding with a detection label or with a capture agent or other moiety. A single measure of binding (e.g., based on fluorescence of the detection label) will therefore necessarily include both specific binding and non-specific binding components and result in overestimation of the degree of specific binding. In some cases, a signal may be present due to non-specific interactions alone without any specific component. However, a single measure of binding will not be able to distinguish between a true (specific) signal, a false (non-specific) signal, or a mix of both.

Furthermore, non-specific binding can often be relatively stable over time. This leads to significant complications and limitations for applications such as biomarker discovery and validation, wherein non-specific signals can taint results and lead to the expensive and lengthy pursuit of biomarkers that are ultimately determined to be of no value or significance. Additionally, in clinical diagnostic settings, non-specific data leads to higher false positive rates, and limits the ability to accurately quantify biomarker concentrations.

BRIEF DESCRIPTION OF THE INVENTION

Embodiments of the invention relate generally to macro and small molecule detection and, more particularly, to methods for detecting macro and small molecules, including biomolecules, in a liquid or gaseous sample. Methods according to embodiments of the invention are useful in the identification, discovery, and validation of biomarkers, as well as the screening of individuals for such biomarkers for diagnostic, therapeutic, and forensic purposes.

In one embodiment, the invention provides a method of detecting an analyte in a fluid sample, the method comprising: passing a fluid sample containing a labeled analyte across at least one assay surface containing a capture agent for the analyte; detecting the labeled analyte; repeating the passing and detecting steps at least once; and creating a binding curve for the analyte based on the detecting of the labeled analyte. As used herein, an "analyte" refers to a molecule specifically targeted by the capture agent in a given assay, e.g. an antigen (analyte) being targeted by its antibody pair (capture agent), or vice versa.

In another embodiment, the invention provides a method of detecting an analyte in a fluid sample, the method comprising: passing a fluid sample containing a labeled analyte across at least one assay surface containing a capture agent for the analyte; passing a non-labeled solution across the at least one assay surface; detecting the labeled analyte; repeating the passing steps and the detecting step at least once; and creating a binding curve for the analyte based on the detecting of the labeled analyte.

In still another embodiment, the invention provides a method of detecting an analyte in a fluid sample, the method comprising: passing a fluid sample containing an analyte across at least one assay surface containing a capture agent for the analyte; passing a solution containing a labeled molecule across the at least one assay surface, the labeled molecule being capable of binding to the analyte; passing a non-labeled solution across the at least one assay surface; detecting the labeled molecule; repeating the passing steps and the detecting at least once; and creating a binding curve for the analyte based on the detecting of the labeled molecule.

In yet another embodiment, the invention provides a method of distinguishing specific binding of an analyte and capture agent from non-specific binding of the analyte and/or the capture agent, the method comprising: obtaining a binding curve for a given capture agent and its interaction with the sample based on a plurality of temporally-spaced detections of the capture agent to sample binding interactions within an assay (e.g. by measuring the intensity of an optical label directly or indirectly attached to the analyte and/or non-analytes within the sample binding to said capture agent, or by measuring the binding of the analyte and/or non-analytes using any known or later-developed method or technique); determining a first detection intensity of the capture agent to sample binding interactions and a first temporal point in the binding curve at which a rise to an equilibrium may be inferred; and attributing to non-specific binding a first portion of at least one detected intensity subsequent to the first temporal point that is equal to the first detection intensity.

In still another embodiment, the invention provides a method of distinguishing specific binding of an analyte and capture agent from non-specific binding of the analyte and/or the capture agent, the method comprising: obtaining a binding curve for an analyte based on a plurality of temporally-spaced detections of the capture agent to sample binding interactions within an assay (e.g. by measuring the intensity of an optical label directly or indirectly attached to the analyte and/or non-analytes within the sample binding to said capture agent, or by measuring the binding of the analyte and/or non-analytes using any known or later-developed method or technique); determining a first detection intensity of the capture agent to sample binding interaction and a first temporal point in the binding curve at which a rise to an equilibrium has been reached; and attributing the first detection intensity to non-specific binding.

In yet another embodiment, the invention provides a method of identifying biomarkers for therapeutic and/or diagnostic use, the method comprising: obtaining a binding curve for an analyte based on a plurality of temporally-spaced detections of the capture agent to sample binding interactions within an assay (e.g. by measuring the intensity of an optical label directly or indirectly attached to the analyte and/or non-analytes within the sample binding to said capture agent, or by measuring the binding of the analyte and/or non-analytes using any known or later-developed method or technique); determining a first detection intensity of the capture agent to sample binding interactions and a first temporal point in the binding curve at which a rise to an equilibrium may be inferred; attributing to non-specific binding a first portion of at least one detected intensity subsequent to the first temporal point that is equal to the first detection intensity; attributing to specific binding of the analyte a second portion of at least one detected intensity subsequent to the first temporal point equal to a difference between the at least one detected intensity and the first detection intensity; and determining an initial concentration of the analyte based on the specific binding.

In still another embodiment, the invention provides a method of measuring a biomarker concentration in a biological sample of an individual, the method comprising: obtaining from an individual a biological sample; creating a binding curve for a biomarker within the biological sample; determining a first detection intensity and a first temporal point in the binding curve at which a rise to an equilibrium may be inferred; attributing to non-specific binding of the capture agent a first portion of at least one detected intensity subsequent to the first temporal point that is equal to the first detection intensity; attributing to specific binding of the capture agent to the biomarker a second portion of at least one detected intensity subsequent to the first temporal point equal to a difference between the at least one detected intensity and the first detection intensity; and determining an initial concentration of the biomarker based on the specific binding of the biomarker.

In some embodiments, a method to distinguish specific binding from non-specific binding will be used to identify if a signal in a given assay is the result of a specific binding event, a non-specific binding event, or both. In the event that the signal from a given assay is a result of a specific binding event only, there may not be a first detection intensity and a first temporal point in the binding curve at which a rise to an equilibrium has been reached. In such cases, where equilibrium has not been reached within a predefined period (e.g., 30 minutes, 40 minutes, 50 minutes, 60 minutes, etc.) which may vary based at least in part on the binding kinetics of the assay, and the signal rises at a linear or near linear rate through the assay, that signal may be treated as a specific signal.

In the event that the assay signal is a result of both specific and non-specific binding events, methods according to embodiments of the invention may be used to isolate the specific component of the binding curve from the non-specific component, to improve quantitative analysis of the target analytes (e.g. calculation of initial target analyte concentration).

In another embodiment, the invention provides a method of identifying biomarkers for therapeutic and/or diagnostic use, the method comprising: obtaining a binding curve for an analyte in a sample, based on a plurality of temporally-spaced detections of the capture agent to sample binding interactions within an assay containing the sample (e.g. by measuring the intensity of an optical label directly or indirectly attached to the analyte and/or non-analytes within the sample binding to said capture agent, or by measuring the binding of the analyte and/or non-analytes using any known or later-developed method or technique); determining a first detection intensity and a first temporal point in the binding curve at which a rise to an equilibrium has been reached; attributing to non-specific binding of at least one non-analyte a first portion of at least one detected intensity subsequent to the first temporal point that is equal to the first detection intensity; attributing to specific binding of the analyte a second portion of at least one detected intensity subsequent to the first temporal point equal to a difference between the at least one detected intensity and the first detection intensity; and determining an initial concentration of the analyte in the sample based on the specific binding.

In still another embodiment, the invention provides a method of measuring a biomarker concentration in a biological sample of an individual, the method comprising: obtaining from an individual a biological sample; creating a binding curve for the biomarker, based on a plurality of temporally-spaced detections of the capture agent to sample binding interactions within an assay containing the biological sample (e.g. by measuring the intensity of an optical label directly or indirectly attached to the analyte and/or non-analytes within the sample binding to said capture agent, or by measuring the binding of the analyte and/or non-analytes using any known or later-developed method or technique); determining a first detection intensity and a first temporal point in the binding curve at which a rise to an equilibrium has been reached; attributing to non-specific binding of small and/or macro molecules other than the biomarker a first portion of at least one detected intensity subsequent to the first temporal point that is equal to the first detection intensity; attributing to specific binding of the biomarker a second portion of at least one detected intensity subsequent to the first temporal point equal to a difference between the at least one detected intensity and the first detection intensity; and determining an initial concentration of the biomarker based on the specific binding.

In certain embodiments, an assay may refer to an array of capture agents, specific to target analytes, spotted onto a surface (through any method familiar to those skilled in the art such as using contact or non contact printing devices) in known locations such that the resultant binding interactions of analytes or non-analytes to the capture agent(s) can be detected and analyzed, and in the event an analyte is present, it can be identified through reference to the known capture agent it binds to.

In other embodiments, an assay may refer to an array of a biological sample such as a cell lysate, tissue samples, or fractions thereof, or other biological samples that may be of interest for biomarker discovery, validation or screening; wherein the biological sample is spotted onto a surface at known locations, such that resultant binding interactions of analytes or non-analytes to capture agents within the biological sample can be detected an analyzed, and in the even an analyte of interest is present (e.g. a specific interaction is detected with a given fraction of a cell lysate spotted on a array surface), it can be identified through further examination/analysis of the known spot of the biological sample; e.g. through further analysis of a given fraction of a cell lysate, either through further iterative fractionation and arraying, and/or through mass spectrometry and/or through other methods known to those skilled in the art.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIGS. 1A through 1C show schematic top and side cross-sectional views of a cartridge device and its use according to various embodiments of the invention.

FIGS. 4A through 4C show schematic side cross-sectional views of a cartridge device and its use according to various embodiments of the invention.

It is noted that the drawings of the invention are not to scale. The drawings are intended to depict only typical aspects of the invention, and therefore should not be considered as limiting the scope of the invention. In the drawings, like numbering represents like elements among the drawings.

DETAILED DESCRIPTION OF THE INVENTION

Figure 2:
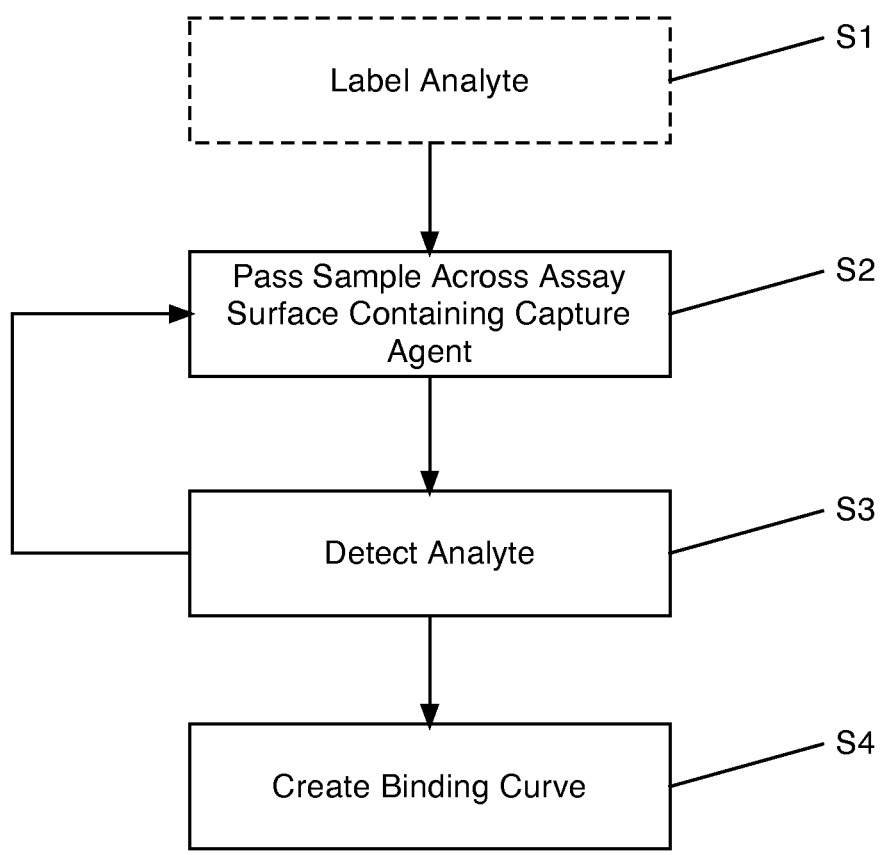
FIGS. 2 and 3 show flow diagrams of various methods according to embodiments of the invention.

Turning now to the drawings, FIG. 1A shows a schematic top view of a cartridge 100 according to an embodiment of the invention. Cartridge 100 includes an assay surface 10 upon which are disposed a plurality of capture agent spots 20-28. Capture agents suitable for use in embodiments of the invention include, for example, antibodies (including autoantibodies), antigens (including native antigens), proteins, peptides, complexes of antibodies and antigens, complexes of proteins, lipids, cell or tissue lysates and fractions thereof, DNA, RNA, and other molecular or elemental moieties or complexes thereof, capable of binding to and forming a complex with an analyte of interest, as will be recognized by one skilled in the art. Capture agent spots 20-28 therefore comprise collections of capture agents adhered to assay surface 10, such that corresponding analytes (e.g., a protein, a peptide, an antibody, an auto-antibody, a native antigen, a protein complex (including complexes of antibodies, antigens, native antigens and autoantibodies), a lipid, DNA, RNA, etc.), when passed across capture agent spots 20-28 will tend to bind to the capture agents, thereby forming an analyte-capture agent complex amenable to detection and measurement. Each capture agent spot 20-28 may include the same capture agent or different capture agents. Similarly, while capture agent spots 20-28 are shown in FIG. 1A in a substantially straight line, other arrangements are also possible and in some cases desirable, as will be described below.

Cartridge 100 includes an inlet 30 and outlet 34 through which an influent 32 and effluent 36, respectively, pass, thereby permitting flow 38 of a sample across assay surface 10 and capture agent spots 20-28. Often, a sample passed through cartridge 100 is in liquid form, although this is not essential. An analyte could, for example, be contained in a gaseous fluid and passed through cartridge 100 in a manner similar to passage of a liquid. Similarly, as will be described in greater detail below, a fluid sample may typically be passed through cartridge 100 under pressure through use of a pump or similar device. As such, a pump and control valve may be connected to inlet 30 and/or outlet 34 such that a fluid sample is passed into inlet 30, across assay surface 10, and out outlet 34 by force (e.g., positive pressure exerted by a pump connected to inlet 30 and/or negative pressure exerted by a pump connected to outlet 34). For purposes of illustration and simplicity only, embodiments of the invention will be described below in the context of analysis of a liquid sample.

FIG. 1B shows a schematic side view of cartridge 100 in use for detection of an analyte according to an embodiment of the invention. A liquid sample containing a labeled analyte 48 is being passed through cartridge 100, forming analyte-capture agent complexes at capture agent spots 20-28. Labeled analyte 48 may be labeled using, for example, a fluorescent label and/or a luminescent, colormetric, or radioactive label. Other known or later-developed labeling methods and techniques may similarly be used in practicing the various embodiments of the invention. For purposes of illustration and explanation only, and without limitation to the scope of the invention, the embodiments of the invention disclosed herein will be described in the context of analytes that have been labeled with a fluorescent label.

An excitation beam 50 is positioned onto capture agent spot 22 to excite a fluorescently-labeled analyte. It will be understood by those skilled in the art that such an excitation beam could be a laser beam that covers a wide area of the array upon exposure, and not just one spot as used for illustrative purposes herein. As shown in FIG. 1B, excitation beam 50 is delivered onto capture agent spot 22 from beneath. It is noted, and would be recognized by one skilled in the art, of course, that excitation beam 50 may be delivered from other positions, including from above and/or the side of capture agent spot 22.

In the embodiment shown in FIG. 1B, excitation occurs during the passage of the labeled analyte 48 through cartridge 100. As a consequence, both free analyte and analyte bound in an analyte-capture agent complex will be excited and contribute to a fluorescent emission 52. That is, fluorescent emission 52 will contain fluorescence originating from both the analyte-capture agent complex and free analyte, the latter constituting background fluorescence that must be accounted for during quantitative analysis. For the sake of simplicity, excitation of and fluorescent emission from only capture agent spot 22 is shown in FIG. 1B. In some embodiments of the invention, each capture agent spot 20-28 will be excited simultaneously or nearly simultaneously. In other embodiments of the invention, excitation of and fluorescent emission from a first capture agent spot or group of capture agent spots will be temporally separated from excitation of and fluorescent emission from a second capture agent spot or group of capture agent spots. This may be desirable, for example, where the first capture agent spot or group of capture agent spots targets analytes labeled with a first fluorescent label and the second capture agent spot or group of capture agent spots targets analytes labeled with a second fluorescent label.

Similarly, as will be recognized by one skilled in the art, the excitation and emission wavelengths will vary based on the fluorescent label(s) used. DYLIGHT® 549 (a fluorescent dye) and DYLIGHT® 647 (a fluorescent dye), for example, commonly used as fluorescent labels, have excitation peaks at 549 nm and 647 nm, respectively.

A longitudinal assay method according to one embodiment of the invention comprises iteratively exciting one or more capture agent spot 20-28 and measuring the resulting fluorescence, as in FIG. 1B, to create a binding curve for the analyte. FIG. 2 shows a flow diagram of an illustrative method for creating such a binding curve according to one embodiment of the invention. An analyte may optionally be labeled at S1, in the case that the analyte is not already labeled. As shown in FIG. 1B, the analyte 48 may be fluorescently labeled, although this is not essential. Other labeling techniques or methods may be used, such as luminescence, colormetric, or radiolabeling.

At S2, a sample, such as a liquid, containing the labeled analyte 48 is passed across an assay surface 10 containing a capture agent (e.g., capture agent spots 20-28). At S3, the labeled analyte 48 is detected. In the case of a fluorescently labeled analyte 48, such detection may be by excitation and measurement of emission, as shown in FIG. 1B. S2 and S3 are iteratively looped at least once to obtain at least two measurements of emission intensity. In practice, S2 and S3 would likely be iteratively looped at least twice to obtain at least three measurements of emission intensity. These measurements of emission intensity (or other measure of intensity if a different labeling method or technique is used) are used at S4 to create a binding curve for the analyte. Binding curves created according to embodiments of the invention, as well as their interpretation, will be described in greater detail below.

Returning to FIG. 1C, another embodiment of the invention is shown. Here, rather than exciting and measuring fluorescent emission (i.e., detecting) while the labeled analyte (48 in FIG. 1B) is passing through cartridge 100, excitation and emission occur during or following the subsequent passage of a non-labeled solution 68, such as a buffer solution. That is, the labeled analyte 48 is passed through cartridge 100 without detection, which occurs later, as shown in FIG. 1C, during or following passage of the non-labeled solution 68. In such an embodiment, fluorescent emission 54 will be free or substantially free of background fluorescence attributable to labeled analyte 48.

Figure 3:
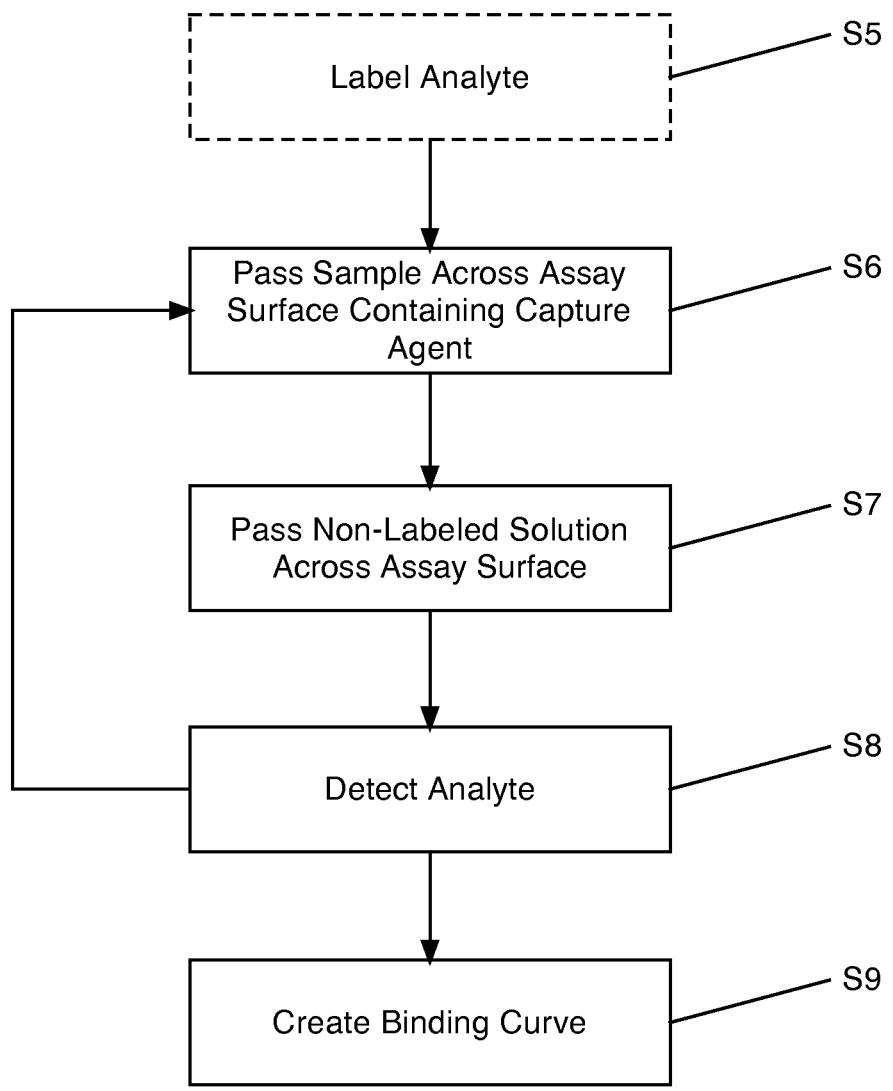

The method of FIG. 1C is shown in the flow diagram of FIG. 3. At S5, an analyte may optionally be labeled, as described above. At S6, a sample containing the labeled analyte is passed across an assay surface containing a capture agent. At S7, a non-labeled solution is passed across the assay surface. At S8, the labeled analyte is detected (e.g., by excitation and measurement of fluorescent emission). As noted above, detecting the labeled analyte at S8 may occur during and/or following passage of the non-labeled solution at S7. S6 through S8 are iteratively looped to obtain at least two detections of the labeled analyte, which are used at S9 to create a binding curve for the analyte. Similarly to as noted above, in practice, S6 through S8 would likely be iteratively looped at least twice to obtain at least three detections of the labeled analyte.

Longitudinal assays according to embodiments of the invention may be carried out in other ways, of course. For example, FIGS. 4A-4C show yet another embodiment of the invention. In FIG. 4A, an unlabeled analyte 78 is passed across assay surface 10, whereupon analyte-capture agent complexes are formed at capture agent spots 20-28. In FIG. 4B, a fluorescently labeled solution 88 is then passed across assay surface 10. In such an embodiment, the fluorescently labeled molecules in the solution 88 bind to or otherwise complex with the analyte or the analyte-capture agent complex, permitting development and quantitation of the analyte. As noted above, while the embodiment described here utilizes a fluorescent label, this is not essential. Other labeling methods and techniques may be similarly employed.

In FIG. 4C, a non-labeled solution, such as a buffer or, in some embodiments of the invention, sample solution containing the unlabeled analyte 78, is again passed across assay surface 10, during and/or following which detection (by excitation 50 and emission 54 measurement) occurs.

Figure 5:
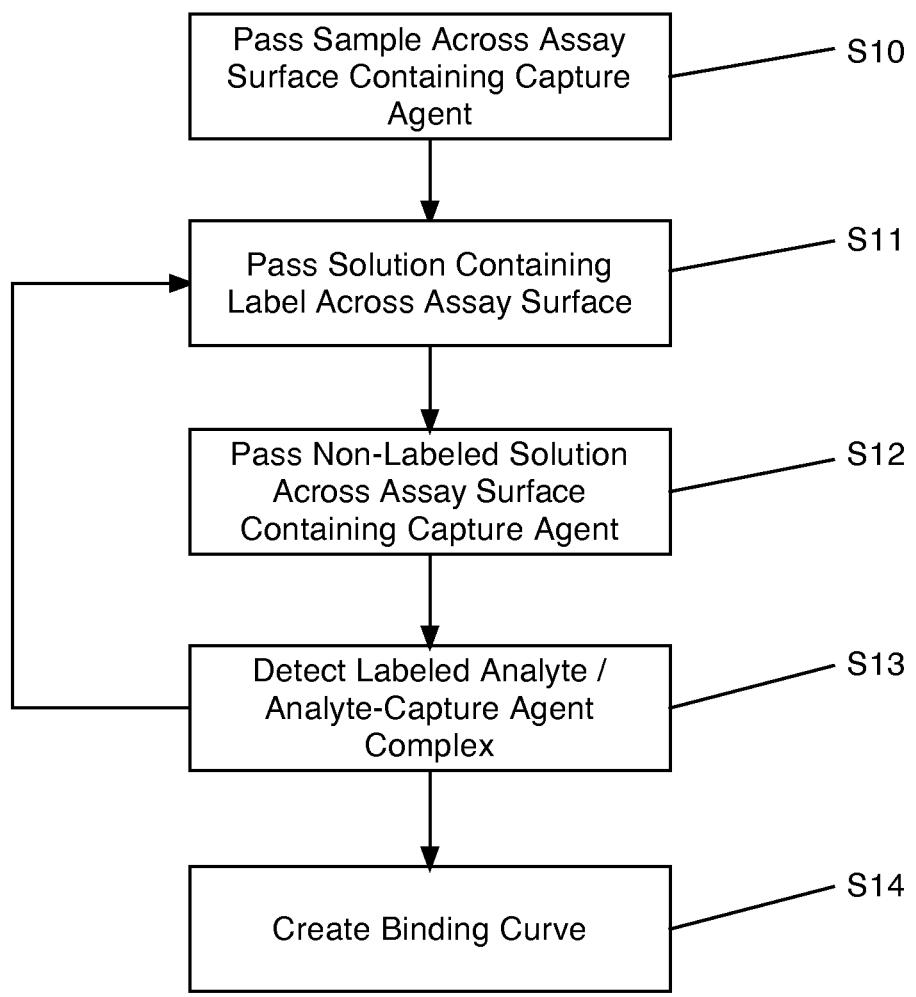
FIGS. 5 and 6 show flow diagrams of various methods according to embodiments of the invention.

A flow diagram of the embodiment of FIGS. 4A-4C is shown in FIG. 5. At S10, a fluid (e.g., liquid) sample containing the unlabeled analyte is passed across the assay surface and capture agent. At S11, a solution containing a label (e.g., fluorescent, luminescent, etc.) is passed across the assay surface and capture agent. At S12, a non-labeled solution, such as a buffer or a sample solution containing the unlabeled analyte, is passed across the assay surface, during or following which the now-labeled analyte or analyte-capture agent complex is detected at S13. S11 through S13 are iteratively looped at least once to obtain at least two detections at S13, from which a binding curve is created at S14. As noted above, S11 through S13 may, in practice, be looped at least twice to obtain at least three detections at S13.

Figure 6:
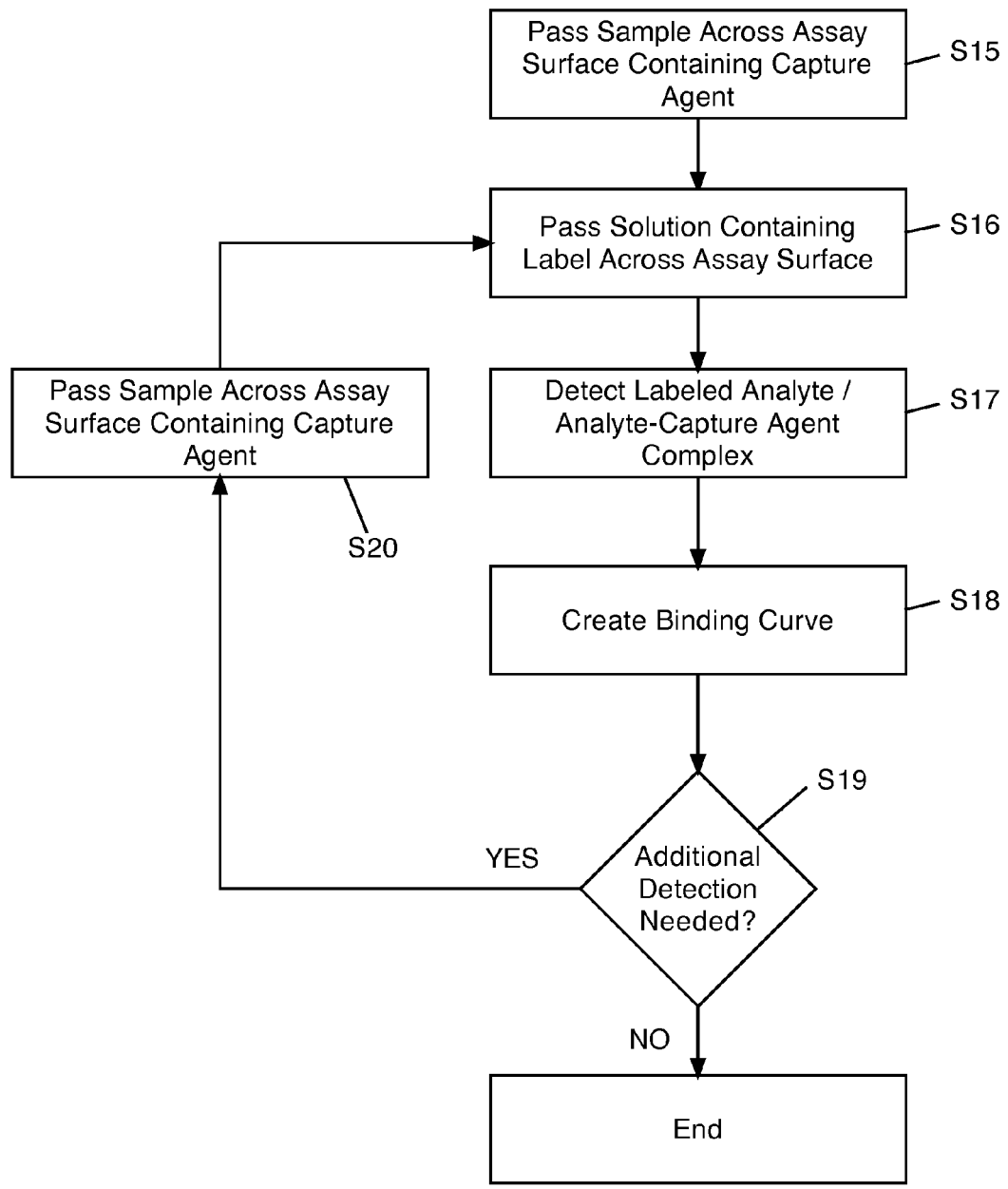

FIG. 6 shows a flow diagram of a method according to yet another embodiment of the invention. At S15, a sample containing an unlabeled analyte is passed across the assay surface containing a capture agent. At S16, a labeled solution is passed across the assay surface. At S17, the analyte and/or analyte-capture agent complex is detected. In some embodiments of the invention, the detection at S17 occurs during passage of the labeled solution at S16, in which case the detected intensity will include background fluorescence attributable to the label contained within the labeled solution, as in the embodiment shown in FIG. 1B. Such background fluorescence may be accounted for during subsequent quantitative analysis.

At S18, a binding curve is created using the detection made at S17. At S19, if an additional detection is needed (e.g., if only a single detection at S17 has been made and the binding curve created at S18 includes only the single detection), an additional sample containing the unlabeled analyte is passed across the assay surface at S20 and S16 through S18 are then iteratively looped. If an additional detection is not needed (e.g., if an additional sample containing the unlabeled analyte has been passed across the assay surface at S20 at least once), the binding curve created during the most recent instance of S18 may be considered a final binding curve and flow may end.

While the methods above describe obtaining at least two detections of a labeled analyte or analyte-capture agent complex for use in creating a binding curve, as noted above, in practice, the number of detections will often be greater. For example, longitudinal assays according to various embodiments of the invention may be conducted over extended observation periods, typically between about 5 and about 120 minutes, with a detection made every minute or two.

In some embodiments of the invention, a detection may be made even more frequently and the longitudinal assay may be conducted over time periods of less than 5 minutes. For example, if the binding kinetics of a particular assay permit detection every 10 seconds or so, enough data may be collected to create a binding curve in less than a minute. As will be recognized by one skilled in the art, the binding kinetics of assays vary considerably. As such, the durations of longitudinal assays according to the various embodiments of the invention will depend, for example, on the frequency at which detections may be made and the number of detections desired for use in creating a binding curve.

As a consequence of the relatively fine grain of the resulting binding curves that may be created according embodiments of the invention, an additional difficulty common to end-point assays, i.e., distinguishing specific binding from non-specific binding, may be overcome, as will be described below.

Figure 7:
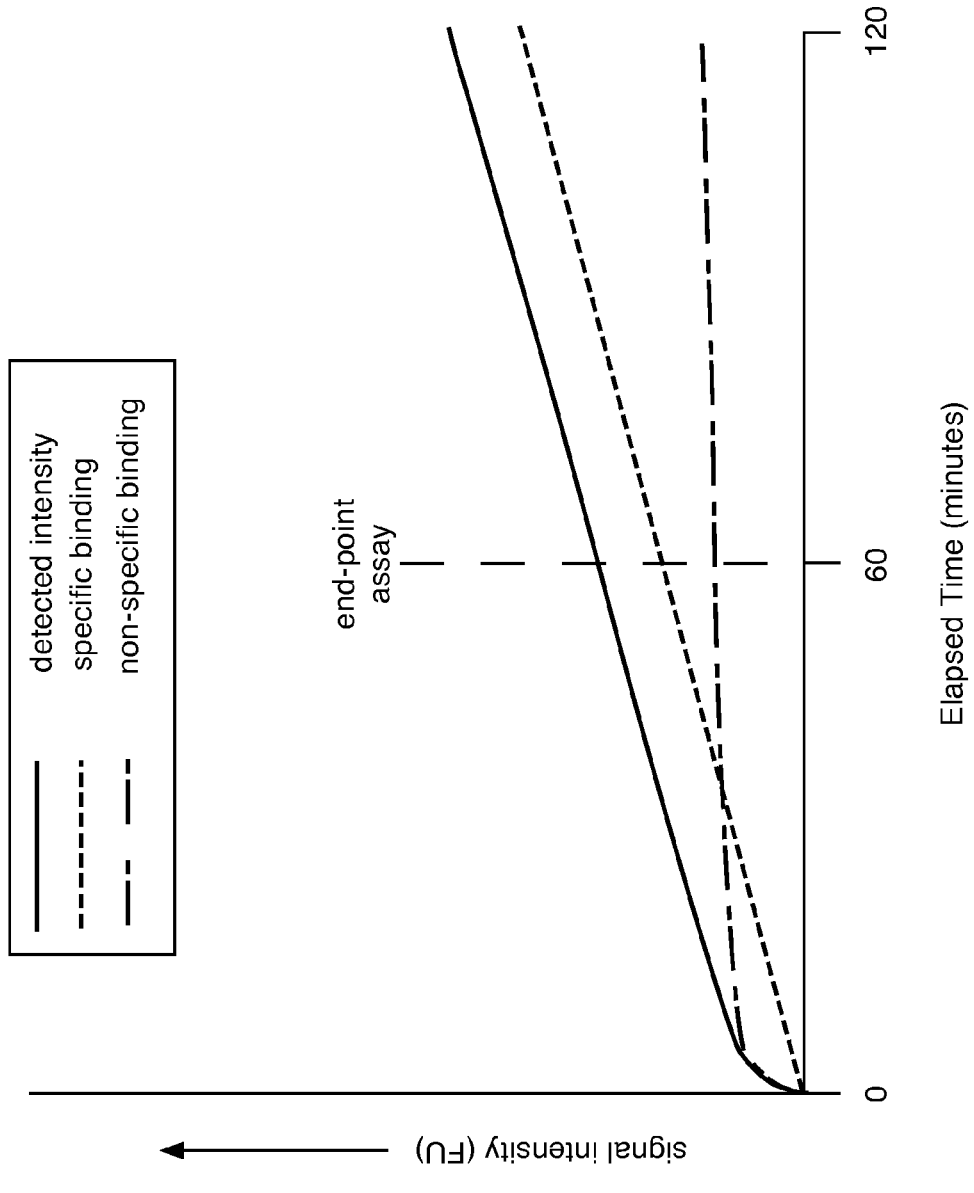
FIGS. 7 through 9 show schematic representations of binding curves created using methods according to various embodiments of the invention.

FIG. 7 shows a simplified binding curve for an analyte, as may be created using a longitudinal assay method according to an embodiment of the invention (or other small or macro molecule screening platforms that can generate a temporal binding curve). As can be seen, the detected intensity exhibits a steep initial rise early in the assay period, followed by a prolonged, substantially linear rise thereafter. The shape of the detected intensity curve is due, in part, to the relative proportion of analyte in a sample, and in part, to the specifics of the concentration corrected binding interactions that are forming the curve.

With a specific binding event, a linear binding curve is observed that typically does not reach equilibrium during the course of the assay (an assay may typically be run for 15 minutes, 30 minutes, 60 minutes, 120 minutes, etc., and will depend on target analytes within the assay and/or the type of assay). The longer the assay is run, the higher the specific signal builds, ultimately approaching the detection platforms maximum intensity, depending on the concentration of the analyte.

In contrast, with a non-specific binding event, a binding curve is observed that typically has a steeper initial gradient and reaches equilibrium (levels off) at an intensity level substantially below the platform's maximum (in some cases at or under $1/20^{th}$ of platform saturation). Furthermore, such non-specific signals rise to equilibrium more rapidly than the specific signals, and typically reach equilibrium during the course of the assay (under 60 minutes, 45 minutes, 30 minutes, etc., and often under 20 minutes or 10 minutes).

Whereas the intensity of the signal from a given binding event does not provide a clear mechanism for distinguishing specific signals and non-specific signals, as at any one time point the intensity level for each may be similar, the behavior of the binding curve does provide a mechanism for such discrimination. Indeed, if a signal from a binding event builds to an equilibrium level that is under $1/10^{th}$ of typical platform saturation levels within 40 minutes, or preferably within 30 minutes, or preferably within 20 minutes, or preferably within 10 minutes (depending on the specifics of the assay), then this signal may be deemed to be the result of a non-specific binding event.

In contrast, if the signal from a given binding event builds throughout the assay in a linear or near linear way, and/or if the signal does not reach equilibrium within an assay period (e.g., within 30 minutes, 40 minutes, 50 minutes, 60 minutes, 90 minutes, or 120 minutes, depending on the assay parameters) the signal is deemed to be the result of a specific binding event.

In the case where both specific and non-specific binding events form the signal, a discrimination method according to an embodiment of the invention can be used to isolate the non-specific component of the binding curve form the specific component of the binding curve. Optionally, using curve fitting software to 'fit' appropriate rate equations to each curve and enable subsequent analysis (e.g., analysis of a combined curve will first see the non-specific component subtracted, then use the 'fitted' rate equation for the specific component to back calculate initial concentration levels of the target analyte).

Some reasons for the observed differences in behavior of binding curves resulting from either non-specific or specific interactions include, but are not necessarily limited to:

1. Concentration differences: For example, in a sample in which the analyte of interest comprises less than 1% of the total sample concentration, as is often the case, binding of the analyte and capture agent and/or binding of the label and analyte will increase gradually in a substantially linear fashion, shown in FIG. 7 as the specific binding component. As used herein, a "low abundance" analyte is any analyte having a relative proportion of less than about $1/10$ of the total sample concentration. Often, the relative proportion of a low abundance analyte is less than about $1/100$. In some cases, particularly where the low abundance analyte is a protein, the relative proportion is less than about $1/1000$ of the total sample concentration.

Contrarily, in a sample in which non-analyte components (e.g., non-analyte proteins, peptides, antibodies, auto-antibodies, native antigens, protein complexes, lipids, DNA, RNA, or other small or macro molecules, etc.) comprise a much greater proportion of the sample, e.g., 10% or more of the total sample concentration, as is often the case, non-specific binding of a non-analyte component and capture agent and/or binding of the label and non-analyte component will increase to equilibrium very rapidly. This is shown in FIG. 7 as the non-specific binding component.

2. Inherent Reaction Rate Differences: As used herein the 'inherent' reaction rate is the rate of the reaction (binding event) after being corrected for concentration differences. Conversely, the reaction rate is the inherent rate multiplied by the concentration of reactants. The 'inherent' reaction rate can also be described as the rate constant in a mathematical equation describing a reaction rate.

Typical capture agent-to-analyte bindings or reactions, e.g. antibody to antigen binding, result through a mix of complementarity in shapes (commonly known as 'lock and key' or 'induced fit' in the case of antibody to antigen binding), hydrophobic interactions, hydrogen bonds, electrostatic, and Van der Waals forces, and, in the cases of some macro or small molecules, binding may result from covalent interactions.

Importantly, the binding of a 'non-specific' interaction is typically both 'weaker' and happens 'faster' than the binding of a 'specific' interaction. More broadly, the binding curve profile of a specific interaction typically differs from that of a non-specific interaction in a given assay. For example, for a specific antibody/antigen pair, the primary component in the binding process is the 'lock and key' or 'induced fit' interaction. Non-specific interactions with either the antibody or antigen will not include this 'lock and key' component. Instead, they will be driven by, for example, Van der Walls forces. Such interactions are typically weaker, occur faster, and disassociate (end) faster, than the more specific 'lock and key' interactions.

Accordingly, such reactions will typically build a signal more rapidly, due to their faster initial binding rates (typically represented by a higher rate constant and 'steeper' initial binding curve), and the signal will also reach equilibrium more rapidly, due to the weaker binding from such reactions, and faster disassociation rates (the rates of binding and disassociation level out after a relatively short time period, e.g. 10 minutes, 20 minutes, 30 minutes, etc., depending on the specifics of the binding kinetics).

Figure 8:
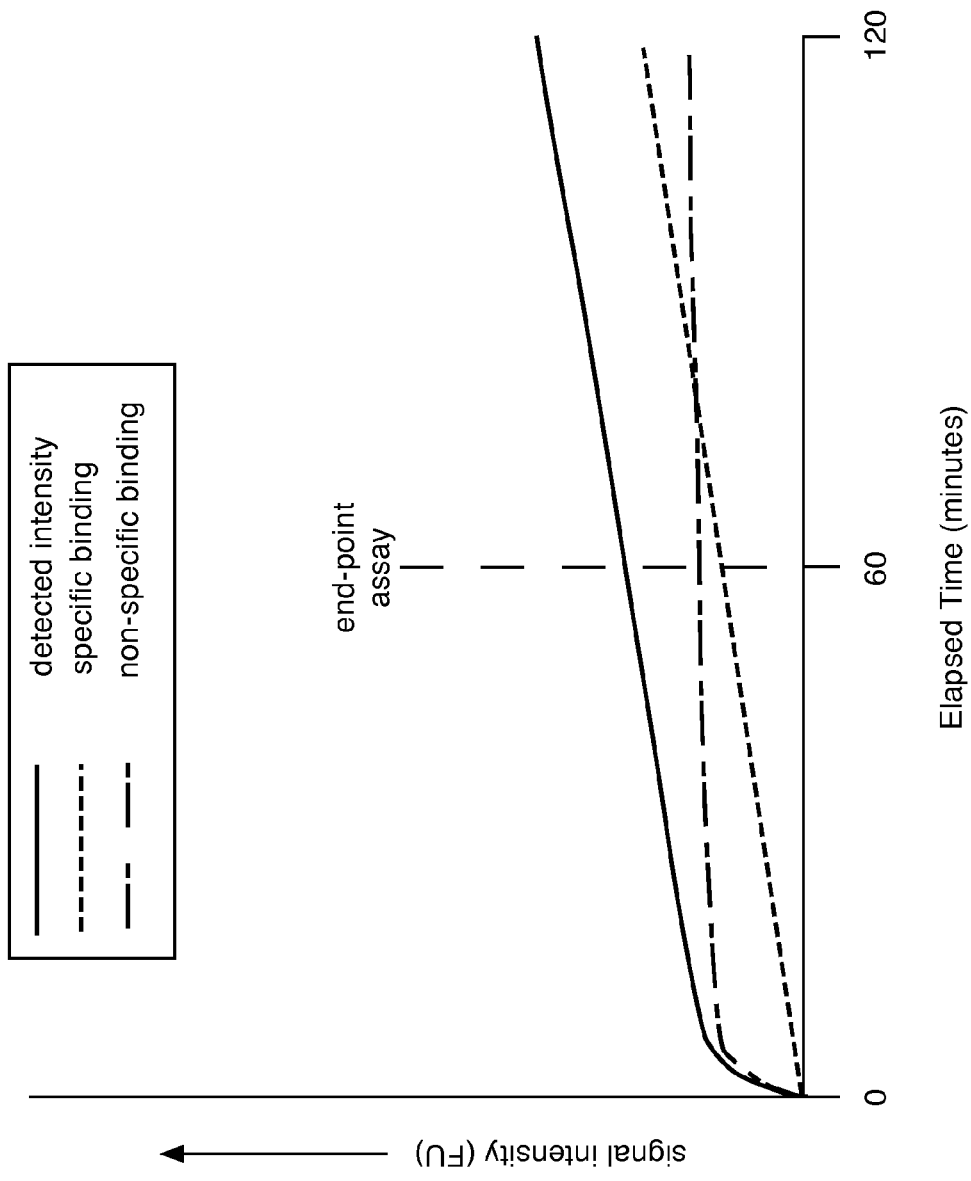
Figure 9:
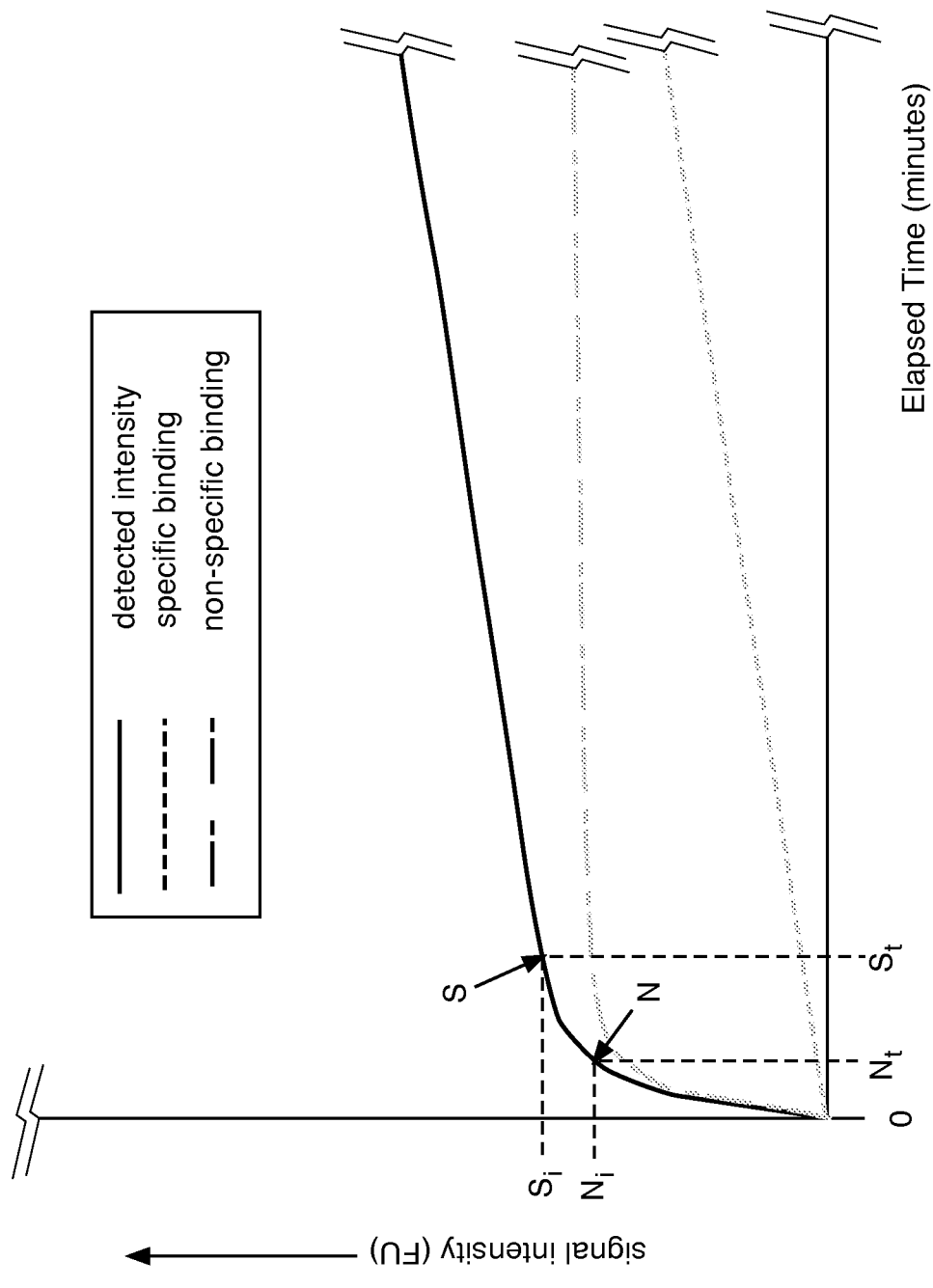

In general terms, a higher rate constant is observed as a 'steeper' binding curve on the plots in FIGS. 7-9. Non-specific binding events produce steeper binding curves which reach equilibrium or saturation more rapidly than will a 'specific' binding event. Specific binding builds more gradually over time (i.e., specific binding has a lower rate constant/gradient), and is represented in FIGS. 7-9 as the shallower curves (lower rate constants), which typically continue to grow in a linear or near linear fashion over the course of the assay, as equilibrium for specific interactions may not be reached during the run time of the assay.

In some cases, the signals detected from an assay will be a combination of both specific binding and non-specific binding, shown as the solid "detected intensity" lines in FIGS. 7-9.

While it is known that a detected intensity will often include both specific and non-specific components, known end-point assay methodologies preclude distinguishing these components. For example, using a known end-point assay, only a binding "snapshot" will be obtained, as shown in FIG. 7 at 60 minutes. Using such a methodology, a single point (and therefore a single value) along the detection intensity curve will be obtained. The specific binding and non-specific binding components of that value are unknown and cannot be determined using known end-point assay methods.

Thus, when employing such a known method, one is left to assume that the true value of the specific binding component is less than the detected intensity. Because one cannot know the extent of the non-specific binding component, however, one cannot know how much lower the specific binding value is from the detected intensity. Differences in sample constitution, the binding kinetics of various analytes, and other variables can lead to large differences in the relative proportions of the non-specific binding components, making the assumptions required in using known end-point assays highly unreliable.

For example, FIG. 8 shows a binding curve in which the non-specific component is proportionally much greater than in FIG. 7. This may be attributable, for example, to the sample comprising a smaller proportion of analyte and a larger proportion of non-analyte components. In some cases, a signal will be the result of non-specific binding only, as none of the target analyte is detectible. This may be because it is not present, or not present in high enough concentration to be detected, in which case the specific component of the combined curve will not be present. Alternatively, in some cases, the signal may arise from specific binding events only, in which case the non-specific component of the combined curve will not be present.

As can be seen in the example of FIG. 8, a known end-point assay at 60 minutes would result in a detected intensity approximately twice as great as the specific binding component. As discussed, in some cases, there may be no specific binding component to a signal, and the observed signal is a result of non-specific binding only. End point or single time point assays offer no mechanism for differentiating such signals. In a clinical setting, partial or total non-specific binding may lead to misdiagnosis of a disease or disorder and/or suboptimal treatment of such a disease or disorder. In a research or discovery setting, partial or total non-specific binding may lead to misidentification and/or pursuit of an analyte that is of little or no clinical, therapeutic, or diagnostic value. It should be noted that the 'binding curve' analysis methodology described herein can be utilized with any platform that collects 'time-course' data, and thus enables the construction of binding curves and the quantification of associated rate constants and analyte concentrations etc. Accordingly, the method is not exclusively limited to the longitudinal assay platform described herein.

FIG. 9 shows a detailed view of a portion of the binding curve of FIG. 8. As can be seen in FIG. 9, at approximately point N in the detected intensity curve, the rapid rise in signal intensity, attributable primarily to non-specific binding, has begun to slow as the non-specific binding approaches equilibrium. Thus, one can infer the equilibrium point of the non-specific binding at an approximate signal intensity $N_i$ and elapsed time $N_t$. Thus, one can determine or approximate the specific binding component of the detected intensity by subtracting from the detected intensity value at any time greater than $N_t$, the value of $N_i$.

Similarly, at approximately point S, a substantially linear rise in the detected intensity curve begins. This substantially linear rise is primarily or exclusively attributable to the specific binding component. Point S corresponds to a signal intensity $S_i$ and elapsed time $S_t$, which are greater than $N_i$ and $N_t$, respectively.

As will be apparent to one skilled in the art, known end-point assays provide insufficient data to differentiate signals caused by specific binding from those caused by non-specific binding; neither can they differentiate the specific binding and non-specific binding components of the detected intensity where a signal contains components of each. An effective real-time longitudinal assay according to an embodiment of the invention, however, permits such differentiation.

Figure 10:
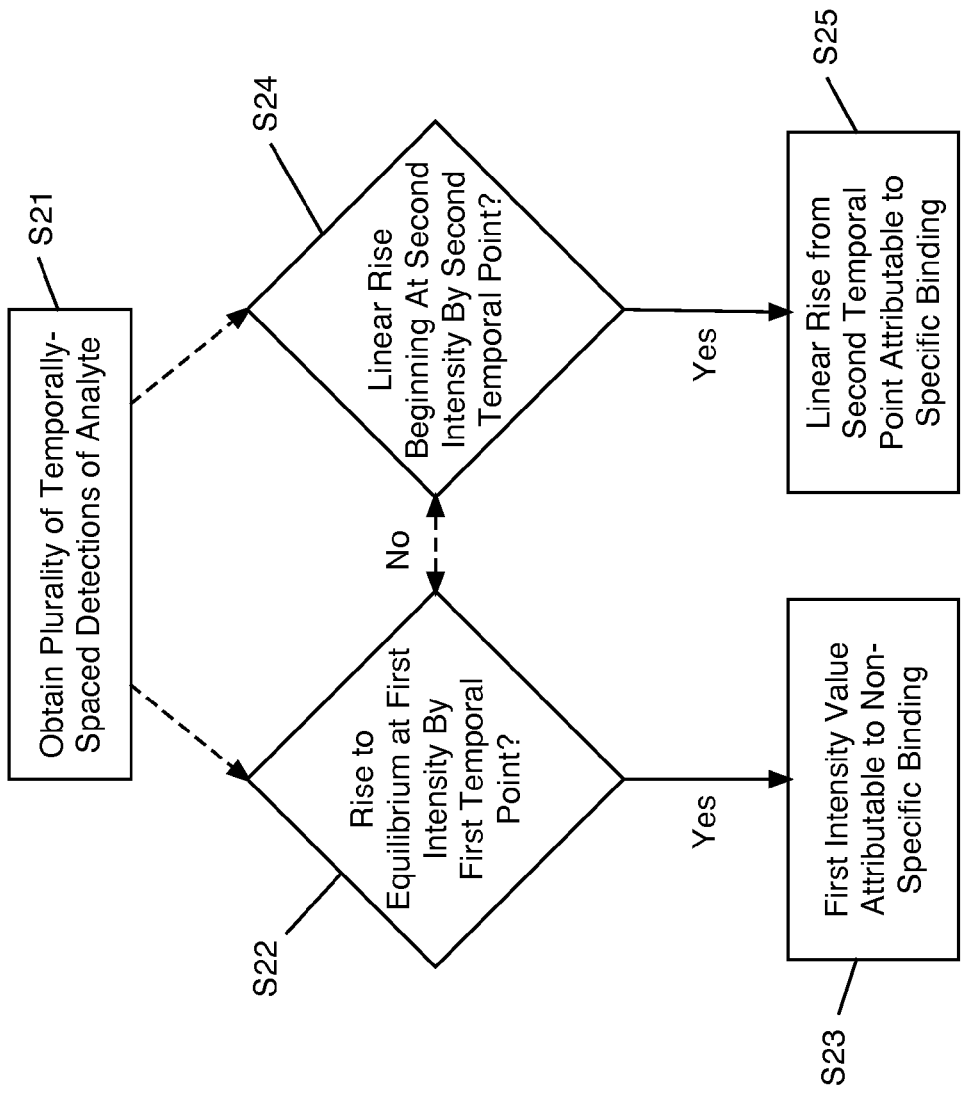
FIG. 10 shows a flow diagram of a method according to an embodiment of the invention.

FIG. 10 shows a flow diagram of a method of differentiating specific binding and non-specific binding using a longitudinal assay binding curve according to an embodiment of the invention. At S21, a plurality of temporally-spaced detections of a capture agent to sample binding interactions are obtained, as described above, for example. As noted above, such a plurality of detections may include as few as two detections but may more typically include between about 5 and about 20 detections. In some embodiments of the invention, such a plurality may include more than about 100 detections.

At S22, it is determined whether the binding curve includes a rise to equilibrium at a first intensity by a first temporal point. If so (i.e., Yes at S22), the first intensity value may be attributed to non-specific binding at S23. As described above, the first intensity value may then be subtracted from intensity values at later temporal points to determine or approximate a specific binding intensity value.

It should be noted, of course, as described above with respect to FIG. 9, that the equilibrium at S22 is an inferred equilibrium. That is, referring again to FIG. 9 for purposes of illustration, the equilibrium is inferred to be at intensity $N_i$, which is reached at temporal point $N_t$. In other words, in the case that the binding curve represents both specific binding and non-specific binding, the non-specific equilibrium or saturation point is inferred from a change in gradient or a change in rate constant. This can be seen in FIG. 9 at $N_i$ and $N_t$, where the slope of the measured intensity decreases.

If a rise to equilibrium at a first intensity by a first temporal point cannot be determined (i.e., No at S22), it may be determined at S24 whether a linear or near linear rise begins at a second intensity by a second temporal point. If so (i.e., Yes at S24), the linear or near linear rise from the second temporal point may be attributed to specific binding, as described above.

As noted above, of course, it is possible that a binding curve will not represent any non-specific binding, i.e., all of the binding, or at least all of the measured binding, is specific binding. In such a case, the linear or near linear rise determined at S24 may, in fact, comprise all of the binding curve and a change in gradient or rate constant will not be observed.

On the other hand, it is also possible that a binding curve will not represent any specific binding, i.e., all of the binding, or at least all of the measured binding, is non-specific. In such a case, as noted above, it is likely that a true equilibrium will be reached within the assay period and no linear or near linear rise in measured intensity will be observed.

It should be noted that following S21, either or both paths from S22 and S24 may be followed. That is, the determinations at S22 may be made in the alternative, in combination, or sequentially. Thus, in the case that flow passes initially from S21 to S24, if a linear rise at a second intensity by a second temporal point cannot be determined (i.e., No at S24), flow may pass to S22.

Embodiments of the invention may be employed in any number of clinical, research, discovery, or developmental contexts. For example, in discovery contexts, rapidly distinguishing specific and non-specific binding in a detected intensity may be used in identifying and validating new biomarkers for therapeutic and/or diagnostic use. Such rapid distinguishing may be used to dramatically enhance the discovery process by only passing 'real' signals through to subsequent research and bio-informatics analysis.

In a clinical context, embodiments of the invention may be used to screen for known biomarkers as part of a clinical diagnostic test, whereby accurately quantifying true biomarker concentrations (i.e., the specific binding component) enables more accurate and specific diagnosis. In such contexts, embodiments of the invention may also lower costs by lowering sample requirements.

As noted above, it may be beneficial in some cases to make a determination of an initial concentration of an analyte. For example, in most discovery contexts, analytes of interest will be of low abundance (i.e., less than about 1/10, more likely less than about 1/100, and still more likely less than about 1/1000 of the total initial sample concentration).

One method of determining an initial concentration of an analyte, which may be employed in various embodiments of the invention, includes measuring a rate constant from a known concentration standard. This may be done at the same time as or prior to the collection of specific and non-specific binding data, using the same instrument parameters. The known data are fit to an equation to relate signal intensity to concentration. An initial concentration of the analyte may then be determined by relating a concentration at a time point to an initial concentration.

The quality of an initial concentration determined according to the method above may be determined by examining the quality of the data fit between the known and unknown concentrations. In essence, this is a measure of how well the real data fit the calculated data using the "best fit" parameters. With each increasing time point in a time course experiment, this measure can be recalculated to determine when an acceptable quality measure is met. Once met, data collection may cease. A minimum of three time course data points beyond time zero are necessary, since fitting to two data point will always give a 100% fit.

Furthermore, where binding curves are made up of a specific and non-specific component, two curves will need to be 'fitted' and two rate constants calculated to facilitate the specific to non-specific binding calculations.

Other methods, including methods employing equations other than those referred to above, may be employed in calculating the rate constant and an initial concentration of an analyte, as will be known to one skilled in the art. Such other methods and equations are within the scope of the invention, the above method being provided merely for the sake of illustration.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any related or incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of detecting and determining a concentration of a labeled analyte in a fluid sample, the method comprising:
    passing the fluid sample containing the labeled analyte across at least one assay surface containing a capture agent for the labeled analyte;
    detecting the labeled analyte and determining a first detection intensity at a first temporal point;
    repeating the passing and detecting steps at least once using the same fluid sample and determining at least one additional detection intensity at at least one additional temporal point;
    creating a binding curve for the labeled analyte including the first and at least one additional detection intensities; and
    determining a concentration of the analyte in the fluid sample based on a comparison of the first detection intensity and the at least one additional detection intensity in the binding curve.

2. The method of claim 1, wherein the analyte and the capture agent are each independently selected from a group consisting of: a protein; a peptide; an antibody; an auto-antibody; an antigen; a native antigen; a protein complex comprising a complex of a protein and at least one of the following: an antibody, an antigen, a native antigen, or an auto-antibody; a lipid; DNA; and RNA; and wherein the capture agent may further comprise a cell or tissue lysate or fractions thereof.

3. The method of claim 1, wherein the labeled analyte is labeled with at least one of the following: a fluorescent marker, a luminescent marker, a colormetric marker, or a radioactive marker.

4. The method of claim 1, wherein the fluid sample is a liquid.

5. The method of claim 1, wherein the detecting occurs during the passing of the fluid sample.

6. The method of claim 1, wherein the detecting occurs after the passing of the fluid sample.

7. The method of claim 1, wherein repeating the passing and detecting steps at least once includes repeating the passing and detecting steps between about 5 times and about 20 times.

8. The method of claim 1, further comprising:
    distinguishing specific binding from non-specific binding in the detected labeled analyte using the binding curve and/or a constant associated with the binding curve.

9. The method of claim 8, wherein the distinguishing specific binding from non-specific binding comprises:
    determining a first detection intensity and a first temporal point at which a rise to an equilibrium may be inferred; and
    attributing to non-specific binding a portion of at least one detected intensity subsequent to the first temporal point that is equal to the first detection intensity.

10. The method of claim 9, wherein distinguishing specific binding from non-specific binding further includes:
    subtracting from a second detection intensity the value of the first detection intensity; and
    attributing to specific binding a remaining portion of the second detection intensity, wherein the second detection intensity is greater than the first detection intensity and the second detection intensity occurs at a second temporal point that is subsequent to the first temporal point.

11. The method of claim 8, wherein distinguishing specific binding from non-specific binding includes:
   determining a first detection intensity and a first temporal point at which a rise to an equilibrium has been reached; and
   attributing the first detection intensity to non-specific binding.

12. The method of claim 11, wherein distinguishing specific binding from non-specific binding further includes:
   attributing detection intensities occurring subsequent to the first temporal point to non-specific binding; and
   concluding that the detection intensities of the binding curve do not include a specific binding component.

13. A method of detecting and determining a concentration of an analyte in a fluid sample, the method comprising:
   passing the fluid sample containing the analyte across at least one assay surface containing a capture agent for the analyte;
   passing a solution containing a labeled molecule across the at least one assay surface to label at least a portion of the total analyte in the fluid sample, the labeled molecule being capable of binding to the analyte;
   passing a non-labeled solution across the at least one assay surface;
   detecting the labeled molecule and determining a first detection intensity at a first temporal point;
   repeating the passing steps and the detecting at least once using the same fluid sample and determining at least one additional detection intensity at at least one additional temporal point;
   creating a binding curve for the analyte including the first and at least one additional detection intensities; and
   determining a total concentration of the labeled and unlabeled analyte in the fluid sample based on a comparison of the first detection intensity and the at least one additional detection intensity in the binding curve of the labeled molecule.

14. The method of claim 1, further comprising:
   passing a non-labeled solution across the at least one assay surface.

15. A method of detecting and determining a concentration of an analyte in a fluid sample, the method comprising:
   passing the fluid sample containing the analyte across at least one assay surface containing a capture agent for the analyte;
   passing a solution containing a labeled molecule across the at least one assay surface, the labeled molecule being capable of binding to the analyte;
   detecting the labeled molecule and determining a first detection intensity at a first temporal point;
   repeating each of the passing steps and the detecting step at least once and determining at least one additional detection intensity at at least one additional temporal point;
   creating a binding curve for the analyte including the first and at least one additional detection intensities; and
   determining a concentration of the analyte in the fluid sample based on a comparison of the first detection intensity and the at least one additional detection intensity in the binding curve.

16. The method of claim 15, further comprising:
   passing a non-labeled solution across the at least one assay surface after passing the fluid sample across the at least one assay surface.

17. The method of claim 15, further comprising:
   passing a non-labeled solution across the at least one assay surface after passing the solution containing the labeled molecule across the at least one assay surface.

* * * * *